United States Patent [19]
Davidson

[11] Patent Number: 5,348,026
[45] Date of Patent: Sep. 20, 1994

[54] OSTEOINDUCTIVE BONE SCREW

[75] Inventor: James A. Davidson, Germantown, Tenn.

[73] Assignee: Smith & Nephew Richards Inc., Memphis, Tenn.

[21] Appl. No.: 953,475

[22] Filed: Sep. 29, 1992

[51] Int. Cl.$^5$ .................. A61B 19/00; A61F 2/02; A61F 2/28; A61F 2/30
[52] U.S. Cl. .................. 128/898; 128/897; 623/11; 623/16; 623/18; 623/901; 606/60; 606/65; 606/66; 606/73
[58] Field of Search .............. 623/16, 18, 11, 901; 606/60, 65, 66, 67, 72, 73; 128/897, 898

[56] References Cited
U.S. PATENT DOCUMENTS

| | | | |
|---|---|---|---|
| 3,636,956 | 1/1972 | Schneider | 606/224 X |
| 4,052,988 | 10/1977 | Doddi et al. | 623/66 X |
| 4,743,257 | 5/1988 | Tormala | 623/16 |

Primary Examiner—David Isabella
Assistant Examiner—Dinh X. Nguyen
Attorney, Agent, or Firm—Pravel, Hewitt, Kimball & Krieger

[57] ABSTRACT

A bone screw and its method of manufacturing provides a low modulus osteoinductive bone screw with a high resistance to insertion torquing. The method includes the steps of pre-torquing a plurality of reinforcing fibers, molding a polymer matrix to bond with the pre-torqued fibers, and wherein the screw apparatus is coated with an osteoinductive material such as BMP, growth factors, hydroxyapatite or calcium phosphate.

22 Claims, 2 Drawing Sheets

OSTEOINDUCTIVE BONE SCREW

BACKGROUND OF THE INVENTION

1. Field Of The Invention

The present invention relates to surgical devices, namely orthopedic bone screws and more particularly to a high torque, low modulus, osteoinductive bone screw article and a method of making said bone screw wherein the screw is polymeric with an interval fiber reinforcement, the fibers being pre-torqued prior to and during a curing or molding with a polymer matrix. The polymer matrix is used to bond with the pre-torqued fibers in the shaft and head regions of the bone screw, and the outer surface of the pre-torqued fiber reinforced polymer screw can be coated with an osteoinductive material such as BMP, growth factors, hydroxyapatite or calcium-phosphate material.

2. General Background

Metal bone screws are routinely used to attach bone plates or to fix fractured bone fragments or tissue to bone. Most commonly used are bone screws made of 316L stainless steel. Stainless steel has an elastic modulus of about thirty (30) million p.s.i. significantly greater than that of cortical bone (about two (2) million p.s.i.). The presence of a hole in cortical bone acts as a stress concentrator and can weaken the bone. For example, Edgerton, et al. (J. Ortho. Res., 8,851–855, 1990) have shown that a hole size equal to twenty (20) percent of the bone diameter can reduce torsional strength by about thirty four percent (34%).

When steel screws are removed from plated femurs or tibias after fracture healing, the bone often fractures at the open hole remaining upon removal of the screw. Although the tendency for bone fracture may be less with the steel screw in the bone (i.e. filling the hole) the mismatch in elastic modulus between the steel screw and bone can still produce a certain level of stress concentration. A low modulus screw could be left in place and not allow stress shielding of the bone from the presence of the bone plate. The plate (even metal) would maintain acceptable axial and torsional motion at the bone fracture for healing, but because the attachment screws are of low modulus, flexion of the screw can occur allowing load to transfer through the healed bone in a near-normal fashion. Thus a second surgery to remove the device and screws would not be necessary. A bone screw of low modulus poses a smaller stress concentrator in the bone, thus bone integrity would be similar to that of bone without the bone screws present.

To further assure a minimal or nonexistent reduction in bone strength from the presence of the low modulus screw, the screw or other type of anchoring device could be coated or bonded with BMP, growth factors, hydroxyapatite or another effective osteoinductive (osteogenic) material to fully integrate the surrounding bone with the low modulus screw, further reducing any remaining stress concentration effects.

Various patents have been issued which discuss self-reinforced, absorbable materials having reinforcing elements that are at least partially around some axis pertaining to the implant. For example, U.S. Pat. No. 4,968,317 describes a resorbable material in which the reinforcing elements are formed by fibrillating a sheet of the reinforcing material by drawing it.

U.S. Pat. No. 4,743,257 describes a resorbable material in which the reinforcing elements are parallel threads of the same chemical composition as the rest the implant. U.S. Pat. No. 4,743,257 describes an osteosynthesis composite material which is at least partially absorbable in living tissue. This material comprises an absorbable polymer of copolymer matrix which is reinforced with absorbable polymeric reinforcement elements which have the same chemical element percentage composition as does the matrix. The reinforcing element is shown as parallel threads of polymer. International patent application 90/12550 describes a self-reinforced absorbable surgical material characterized in that the reinforcing elements are wound at least partially around some axis penetrating the implant. The spiral orientation of the reinforcing elements is claimed to allow the screws to resist higher torque forces than known parallel thread or non-reinforced screws.

In surgery it is known to use implants, or their parts or components, which are manufactured at least partially of an absorbable polymer and/or of a polymer composite containing reinforcing elements, for fixation of bone fractures, osteotomies or arthrodeses, joint damages, tendon and ligament damages etc. Such implants are e.g. rods, screws, plates, intramedullary nails and clamps, which have been described in the professional literatures of material technique and medicine.

U.S. Pat. No. 3,620,218, entitled "Cylindrical Prosthetic Devices of Polyglycolic Acid" and U.S. Pat. No. 3,739,733 entitled "Polyglycolic Acid Prosthetic Devices", both issued to E. Schmitt and R. Polistina, describe implants like rods, screws, plates, and cylinders which have been manufactured of polyglycolic acid.

U.S. Pat. No. 4,052,988 issued to N. Doddi, C. Versfelt and D. Wasserman, entitled "Synthetic Absorbable Surgical Devices of Polydioxanone" describes absorbable sutures and other surgical devices manufactured of polydioxanone.

U.S. Pat. No. 4,279,249 issued to M. Vert, F. Chabot, J. Leray and P. Christel, entitled "New Prosthesis Parts, Their Preparation and Their Application" describes osteosynthesis devices which have been manufactured of polylactide or of copolymer containing plenty of lactide units, which matrix has been reinforced with reinforcing elements which have been manufactured of polyglycolide or of copolymer including mainly glycolic acid units.

DE 2947985 A 1, issued to S. Belych, A. Davydov, G. Chromov, A. Moscenskij, I. Movsovic, G. Rojtberg, G. Voskresenskij, G. Persin and V. Moskvitin, entitled "Biodestruktiver Stoff für Verbindungselemente für Knochengewebe" describes at least partially degradable composites which comprise a copolymer of methylmethacrylate and N-vinlpyrrolidone, which has been reinforced with polyamide fibers or with oxycellulose fibers.

U.S. Pat. No. 4,243,775, issued to M. Rosensaft and R. Webb, entitled "Synthetic Polyester Surgical Articles" describes surgical products manufactured of copolymer of glycolic acid and trimethylene carbonate.

U.S. Pat. No. 4,329,743, issued to H. Alexander, R. Parsons, I. Strauchler and A. Weiss, entitled "Bioabsorbable Composite Tissue Scaffold" describes a composite of a bio-absorbable polymer and carbon fibers, which composite is suitable for manufacturing surgical articles.

U.S. Pat. No. 4,343,931, issued to Barrows, entitled "Synthetic Absorbable Devices of Poly(esteramides)" describes absorbable polyesteramides, which are suitable for manufacturing of surgical implants.

Patent Application EPO 0,146,398, issued to R. Dunn and R. Casper entitled "Method of Producing Biodegradable Prosthesis and Products therefrom" describes a method for manufacturing of biodegradable prosthesis about biodegradable polymer matrix which is reinforced with biodegradable ceramic fibers.

WO 86/00533, issued to J. Leenslag, A. Pennings, R. Veth and H. Jansen entitled "Bone Implant" describes an implant material for reconstructive surgery of bone tissue, which material comprises a biodegradable porous polymer material and biodegradable or biostable fibers.

The publication of D. Tunc, "A High Strength Absorbable Polymer for Internal Bone Fixation" 9th Annual Meeting of the Society for Biomaterials, Birmingham, Alabama, Apr. 27–May 1, 1983, p. 17, describes a high strength absorbable polylactide, with an initial tensile strength about 50–60 MPa and which material retains a significant part of its initial strength 8–12 weeks after the implantation. This material can be considered suitable to be applied as basic material in manufacturing of internal bone fixation devices which are totally absorbable in living tissues.

The publication of D. Tunc, M. Rohovsky, W. Lehman, A. Strogwater and F. Kummer entitled "Evaluation of Body Absorbable Bone Fixation Devices" 31st Annual ORS, Las Vegas, Nevada, Jan. 21–24, 1985, p. 165, describes high strength, totally absorbable polylactide (initial strength 57,1 MPa), which was used as plates and screws for fixation of canine radial osteotomies.

The publication of D. Tunc, M. Rohovsky, J. Zadwadsky, J. Speiker and E. Strauss entitled "Evaluation of Body Absorbable Screw in Avulsion Type Fractures", the 12th Annual Meeting of the Society for Biomaterials, Minneapolis-St. Paul, Minn., USA, May 29 to Jun. 1, 1986, p. 168, describes the application of high strength polylactide screws in fixation of avulsion-type fractures (fixation of canine calcaneus osteotomy).

U.S. Pat. No. 4,776,329 issued to R. Treharne entitled "Resorbable Compressing Screw and Method", describes a compression screw comprising a non-absorbable compression parts and a screw. At least the head of the screw comprises material, which is resorbable in contact with tissue fluids.

Self-reinforced absorbable fixation devices have significantly higher strength values than the non-reinforced absorbable fixation devices. U.S. Pat. No. 4,743,257 issued to P. Törmälä, P. Rokkanen, J. Laiho, M. Tamminmäki and S. Vainionpää entitled "Material for Osteosynthesis Devices" describes a self-reinforced surgical composite material, which comprises an absorbable polymer or copolymer, which has been reinforced with absorbable reinforcing elements, which have the same chemical element composition as the matrix.

FI Patent Application No. 87 0111, issued to P. Törmälä, P. Rokkanen, S. Vainionpää, J. Laiho, V.-P. Heponen and T. Pohjonen entitled "Surgical Materials and Devices" describes self-reinforced surgical bone fracture fixation devices which have been manufactured at least partially of fibrillated absorbable material(s).

According to the publication of T. Pohjonen, P. Törmälä, J. Mikkola, J. Laiho, P. Helevirta, H. Lähde, S. Vainionpää and P. Rokkanen entitled "Studies on Mechanical Properties of Totally Biodegradable Polymeric Rods for Fixation of Bone Fractures" VIth International Conference PIMS, Leeuwenhorst Congress Center, Holland, Apr. 12–14, 1989, p. 34/1–34/6, self-reinforced absorbable surgical materials have excellent strength properties, e.g. SR-polyglycolide had bending strength 415 MPa and SR-polylactide 300 MPa.

In the publication of D. Tunc and J. Jadhav entitled "Development of Absorbable Ultra High Strength Polylactide", Am. Chem, Soc., 196th ACS Meeting, Abstracts of Papers, L.A., Calif., Sep. 25–30, 1988, p. 383–387, a good tensile strength (300 MPa) for fibrillated SR-polylactide was measured.

The publication of E. Partio, O. Böstman, S. Vainionpää, H. Pätiälä, E. Hirvensalo, K. Vihtonen, P. Törmälä and P. Rokkanen entitled "The Treatment of Cancellous Bone Fractures with Biodegradable Screws", Acta Orthop. Scand., 59(5), 1988, p. 18, describes the fixation of cancellous bone fractures with self-reinforced absorbable screws, which have a flat head, which head can be located to a slot at the tip of the screwdriver in order to drive the screw into a channel made into the bone.

The following patents relate to absorbable (biodegradable or resorbable) polymers, copolymers, polymer mixtures, or composites: U.S. Pat. No. 3,297,033; U.S. Pat. No. 3,636,956, U.S. Pat. No. 4,052,988; U.S. Pat. No. 4,343,931; U.S. Pat. No. 3,969,152; U.S. Pat. No. 4,243,775; FI Patent Appln. No. 85 5079, FI Pat. Appln. No. 86 0366; FI Patent Appln. No. 86 0440 and FI Pat. Appln. No. 88 5164.

SUMMARY OF THE PRESENT INVENTION

The present invention provides an improved method of manufacturing a low modulus bone screw with a high resistance to insertion torque. The method includes a pre-torquing of a plurality of reinforcing fibers, a polymer matrix is molded to bond with pre-torqued fibers and the screw can be coated with an osteoinductive material.

The bone screw formed by the method of the present invention provides an improved bone screw with an elongated shaft portion, and can have an enlarged head portion at one end of the shaft, the bone screw being coated with an osteoinductive material such as BMP, growth factors, hydroxyapatite, calcium phosphate or the like for example.

The bone screw thus formed by the method of the present invention provides a bone screw with a transverse modulus of elasticity of between about six and fifty GPa, i.e. the effective modulus of the screw when loaded transversely as opposed to longitudinally.

To reduce or eliminate the stress concentration effects of metal bone screws and holes in the bone, to optimize strength of a low-modulus bone screw to allow more reliable insertion and bone fracture stability, and to eliminate the need for a second surgery to remove the implant, a pre-torqued, low-modulus, fiber reinforced polymer matrix bone screw is proposed with or without an hydroxyapatite or other osteogenic material incorporated onto the surface to bond the screw to the bone. A biocompatible high strength fiber and polymer matrix material can be used to construct the bone screw of the present invention described more fully hereinafter.

Fibers are aligned in an uniaxial or longitudinal direction and impregnated with a self-curing or heat curing polymer, or co-mingled with a thermoplastic fiber or powder. The bundle of fibers is passed through an appropriate molding die and fanned out at the top end of the die which is also used to form the head portion of the bone screw.

The fibers at the top are tightly fixed to the die. The fibers are then turned tightly in the direction which will oppose the applied torque during insertion of the final molded bone screw. Fabric and other woven forms of fibers or pre-braided fibers can also be used versus just uniaxial fibers. The torque should be sufficient to allow acceptable insertion into the bone, following molding or curing of the polymer matrix, without failure of the screw head or shaft. The head and thread regions can be finished with pure polymer or random-fiber reinforced polymer.

Because the fibers are pre-torqued in the direction that the torque will be applied during insertion, these fibers will be able to carry the same (or higher) level of torque without breaking when inserted into the bone. Because they are pre-loaded along the screw axis, the screw will be resistant to loading and fracture under the screw head. Circumferentially wound fiber can also be added to the head region to further improve resistance to torque during insertion by the screw driver or like driving implement. Both of these problems currently renders the use of existing resorbable polymer screws to fixation of very low-stress fractures, as screw failure can readily occur.

Because of the low modulus and minimal stress concentration effects, the present pre-torqued bone screw is designed to remain in the bone without the need for a second surgery. Even if a metal bone plate is used, the low modulus neck region of the pre-torqued screw will flex and not allow stress shielding at the healed bone fracture to occur as is the case with current metal screws. Thus even a metal bone plate attached by the pre-torqued bone screws may be left in place and thereby avoiding a second surgery.

Left in place, the low modulus-pretorqued bone screw with a bioactive (osteoinductive) surface will not produce the undesirable level of stress concentration in the bone (and subsequently weaken the bone) as currently produced by metal screws such as stainless steel. Most importantly, the pre-torqued method of manufacture will enable such effective low-modulus bone screws to be reliably inserted into the bone without the high incidence of breakage which limits currently made low-modulus polymer or polymer matrix bone screws.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

Figure 1:
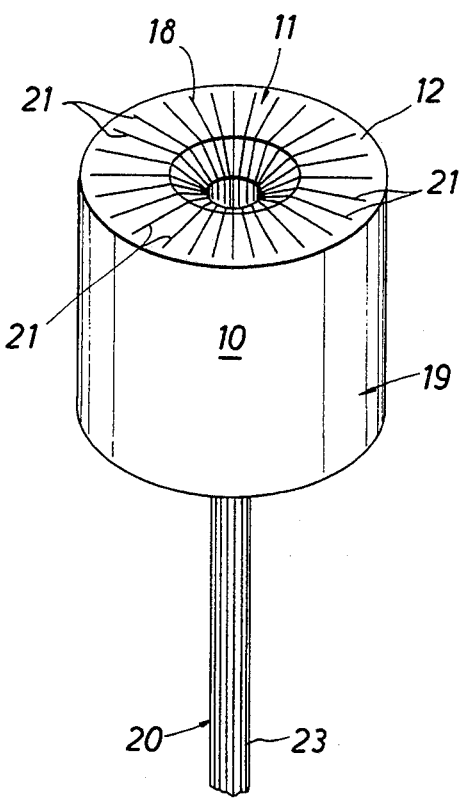
FIG. 1 is a schematic perspective view illustrating the die and fibers used with the method of the present invention, and particularly the step of aligning the fibers in a uniaxial direction in a die.

DETAILED DESCRIPTION OF THE PREFERRED EMBODIMENT:

FIGS. 1–4 illustrate the method of the present invention wherein a low modulus bone screw with high resistance to insertion torquing is formed. In FIG. 1, die 10 is generally cylindrically shaped having a central longitudinal and open ended cavity 11. The die 10 includes an upper flat surface 12 and a lower flat surface 13. Bore 11 is open-ended, communicating with upper opening 14 and lower opening 15.

Figure 2:
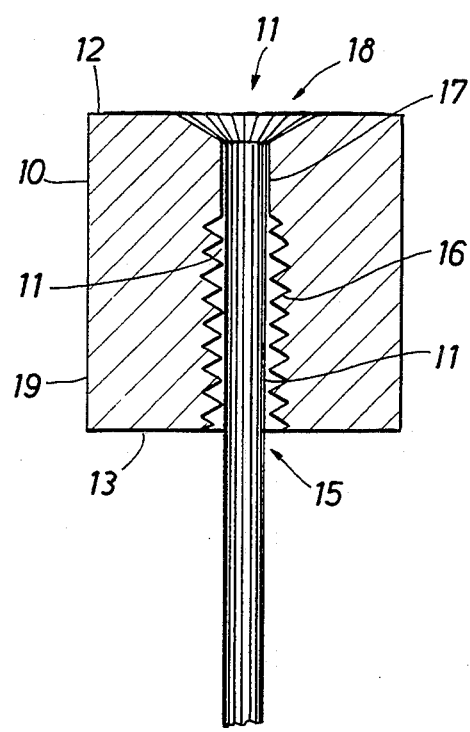
FIG. 2 is a sectional schematic view illustrating the die and the fibers aligned in a uniaxial direction prior to the torquing step of the method of the present invention.
Figure 3:
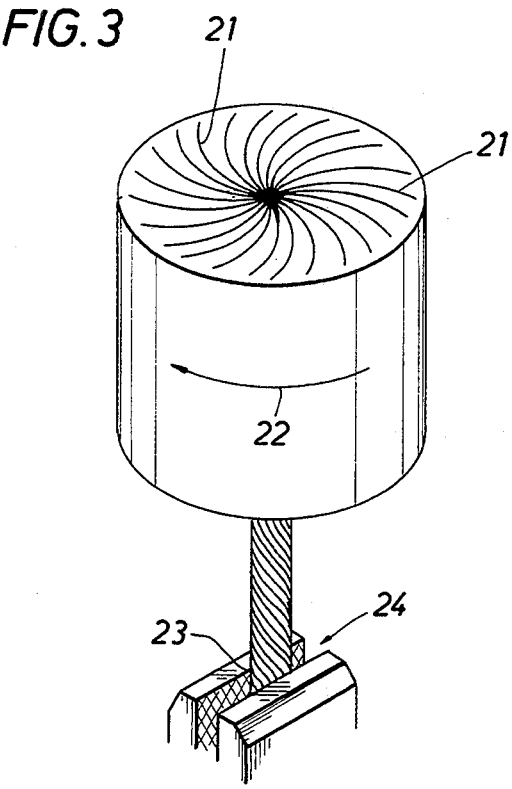
FIG. 3 is a schematic perspective view illustrating the method of the present invention in the twisting of fibers to pre-torque them prior to a molding of a polymer matrix to the pre-torqued fibers.
Figure 4:
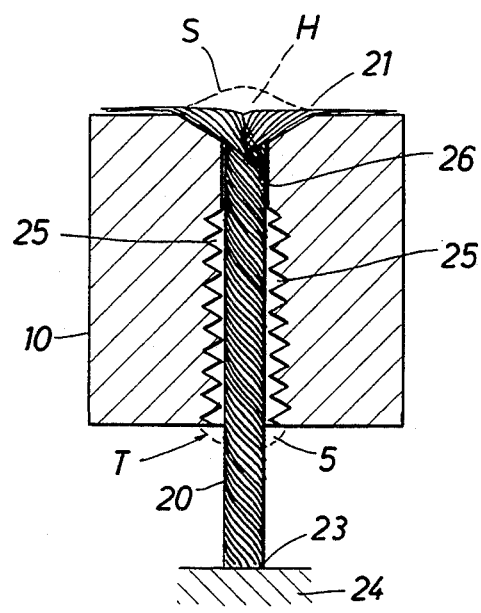
FIG. 4 is a sectional schematic view illustrating the pre-torquing of fibers as part of the method of the present invention.

The cavity 11 of die 10 is shaped to define the shape of the low modulus bone screw which is formed using the method of the present invention. The cavity 11 includes a threaded section 16 with a continuous helical thread pattern for forming a bone screw thread, a cylindrical, unthreaded section 17, and a frustroconical upper section 18 that is designed to form the head of the screw. Die 10 has a generally cylindrically shaped outer wall 19 which can be gripped and turned during a twisting of fibers 20 to pre-torque them to a level acceptable for screw insertion into the bone of a patient during surgery. In FIGS. 1–2, fibers 20 are shown axially aligned and concentrated together in a group. The fibers 20 extend through cavity 11 in the aligned fashion as shown in FIGS. 1 and 2. Fibers 20 are spread out in the frustroconical section 18 that forms the screw head region, with the upper end portion 21 of each fiber 20 radially extending away from cavity 11 and abutting flat surface 12 as shown in FIGS. 1 and 2. Die 10 is then twisted in the direction of arrow 22 (see FIG. 3) while the lower end 23 of fibers 20 are fixed at fixed support 24. In FIG. 4, the circumferentially wound fibers 20 are shown after twisting in order to pre-torque them. The circumferentially wound fibers 20 help absorb the head torque from a screwdriver or like implement as generated during surgical insertion of the bone screw. The head 18 and thread 16 regions of cavity 11 define a space of desired volume for polymer fill between die 10 and fibers 20. In FIG. 4, the space between wound fibers 20 and die 10 is designated by the numeral 25. Bone screw S is outlined in phantom lines in FIG. 4. The bone screw S typically comprises a cylindrical shank portion 26, a helical thread portion as defined by threaded section 16 of die 10, a head portion H, and may have a lower pointed tip T. The shank can comprise an inner most isotropic metallic core integral with the head H, and covered with the low modulus polymer.

Because the fibers are pre-torqued in the direction that the torque will be applied during insertion, these fibers will be able to carry the same (or higher) level of torque without breaking when inserted into the bone. Because they are pre-loaded along the screw axis, the screw will be resistant to loading and fracture under the screw head. Circumferentially wound fiber can also be added to the head region to further improve resistance to torque during insertion by the screw driver or like driving implement. Both of these problems currently renders the use of existing resorbable polymer screws to fixation of very low-stress fractures, as screw failure can readily occur.

Figure 5:
FIG. 5 is a schematic view illustrating test results of the torquing of a simulated bone with an opening in the simulated bone.
Figure 6:
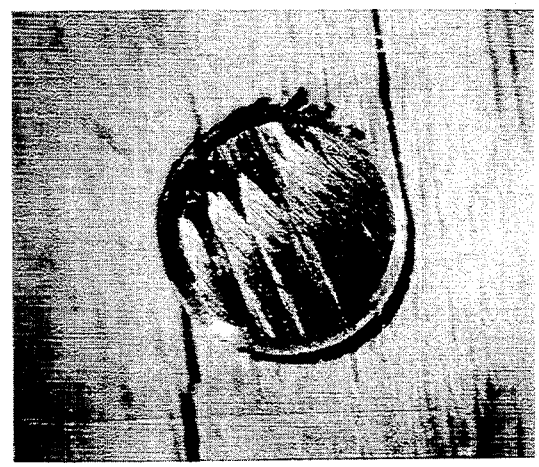
FIG. 6 is a schematic view illustrating test results of the torquing of a simulated bone, and with a metallic bone screw occupying an opening in the bone.
Figure 7:
FIG. 7 is a schematic view illustrating test results of the torquing of a simulated bone, and with a bone screw occupying an opening in the bone wherein the bone screw has a modulus that is similar to that of the bone.

FIGS. 5, 6 and 7 are photographs that demonstrate the results of a torsion test that demonstrates the effect of holes and filled holes on stress concentration. To demonstrate the effect of holes and filled holes on stress concentration, 6 mm diameter holes were drilled in 18 mm diameter wood cylinders (15 cm long) with a wall thickness of 2.5 mm. In one case the hole was left unfilled (FIG. 5). In another case, a hard metal stainless steel dowel was press-fit into the hole (FIG. 6). In the final case, a low modulus (wood) dowel was press-fit and glued (epoxy) into the hole to simulate a bioactive material (hydroxyapatite) coated-low modulus screw (FIG. 7). The samples were loaded in torsion in a Bionix MTS machine and compared to tests in which no hole was present. The wood cylinders were filled with a wood insert (1.5 cm long) for gripping at each end. Results are given below in Table 1, and show the dramatic reduction (48%) in strength due to the hole. Importantly, this reduction in strength is still present with a pressed steel dowel (i.e., bone screw), while the glued, low modulus, wood dowel completely restores the strength.

FIGS. 5, 6, and 7 show clearly how the crack initiates at the hole whether unfilled (FIG. 5) or filled with the tight stainless steel dowel pin (FIG. 6). However, when the pin is an integral part of the wood cylinder, the hole effect can be eliminated and the crack due to torsional loading can initiate anywhere along the cylinder. Notice in FIG. 7 that the crack did not initiate from the hole region.

TABLE 1

RESULTS OF THE TORSION TESTS

| Condition | Average Peak Torque (Nm) | Torsional Energy (Area Under Torque -Rotation Curve) Nm-Deg. | Reduction in Strength |
| --- | --- | --- | --- |
| No hole | 10.3 | 75.7 | — |
| Hole (unfilled) | 7.8 | 39.3 | 48% |
| Hole with steel dowel | 7.0 | 33.2 | 56% |
| Hole with glued wood dowel | 10.7 | 75.4 | <1% |

Perhaps even more important is that a permanent, low-modulus screw with an osteoinductive coating would not necessarily have to be removed.

The following table 2 lists the part numbers and part descriptions as used herein and in the drawings attached hereto.

TABLE 2

PARTS LIST

| PART NO. | DESCRIPTION |
| --- | --- |
| 10 | die |
| 11 | cavity |
| 12 | upper flat surface |
| 13 | lower flat surface |
| 14 | upper opening |
| 15 | lower opening |
| 16 | threaded section |
| 17 | unthreaded section |
| 18 | frustroconical section |
| 19 | die outer wall |
| 20 | reinforcing fibers |
| 21 | upper end portion |
| 22 | arrow |
| 23 | lower end of fibers |
| 24 | fixed support |
| 25 | space |
| 26 | cylindrical shank portion |
| S | bone screw |
| H | head |
| T | lower tip |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of manufacturing a low modulus bone screw with a high resistance to insertion torque, comprising the steps of:
   a) pre-torquing a plurality of reinforcing fibers;
   b) molding a bone screw shaped polymer matrix that includes a shank portion with a helical thread thereon to bond with the pre-torqued fibers;
   c) wherein the fibers are wound in a direction that orients the fibers to resist insertion torque applied to the bone screw; and
   d) wherein in step b) a body is formed having a size and shape of a bone screw.

2. The method of claim 1 further comprising the step of coating the body with an osteoinductive material.

3. The method of claim 1 wherein the body has an elongated shaft with an enlarged head at one end portion of the shaft.

4. The method of claim 2 wherein the osteoinductive material is hydroxyapatite.

5. The method of claim 2 wherein the osteoinductive material is calcium phosphate.

6. The method of claim 1 wherein the modulus of elasticity of the formed low modulus bone screw is between about six and fifty GPa.

7. The method of claim 2 wherein in step c, the osteoinductive material is bonded to the outer surface portion of the body.

8. The method of claim 1 wherein in step "b" the polymer matrix is a biocompatable high strength fiber and polymer matrix.

9. The method of claim 1 wherein in step "a" the fibers are preliminarily aligned in a uniaxial direction.

10. The method of claim 9 wherein in step "b" the polymer is a self-curing polymer.

11. The method of claim 9 wherein in step "b" the polymer is a heat curing polymer.

12. The method of claim 9 wherein in step "b" the polymer is a thermoplastic powder.

13. The method of claim 9 wherein in step "b" thermoplastic fibers are co-mingled with the aligned fibers.

14. The method of claim 1 further comprising the step of forming polymeric threads on the bone screw body.

15. The method of claim 1 further comprising the step of forming fiber reinforced polymer threads on the bone screw body.

16. The method of claim 9 further comprising the step of forming a fiber reinforced head portion on the bone screw body.

17. The method of claim 16 wherein the fiber reinforced head portion includes circumferentially wound fiber reinforcement.

18. The method of claim 9 further comprising the step of coating the screw with an osteoinductive coating.

19. The method of claims 1 or 17 further comprising the step of coating the screw with a porous coating.

20. The method of claim 1 or 9 wherein the fibers are torqued before molding or curing of the polymer matrix.

21. A bone screw article formed according to the method of claim 1.

22. The method of claim 1 wherein the polymer is nonresorbable.

* * * * *